(12) United States Patent
Jenks et al.

(10) Patent No.: US 9,358,385 B2
(45) Date of Patent: Jun. 7, 2016

(54) ALIGNMENT WRAP

(71) Applicants: Julie Jenks, Brentford (GB); Shaun Gayle, Chicago, IL (US)

(72) Inventors: Julie Jenks, Brentford (GB); Shaun Gayle, Chicago, IL (US)

(*) Notice: Subject to any disclaimer, the term of this patent is extended or adjusted under 35 U.S.C. 154(b) by 0 days.

(21) Appl. No.: 14/313,612

(22) Filed: Jun. 24, 2014

(65) Prior Publication Data

US 2015/0335881 A1 Nov. 26, 2015

Related U.S. Application Data

(63) Continuation-in-part of application No. 14/283,354, filed on May 21, 2014.

(51) Int. Cl.
*A61N 1/05* (2006.01)

(52) U.S. Cl.
CPC ............ *A61N 1/0558* (2013.01); *A61N 1/0502* (2013.01)

(58) Field of Classification Search
None
See application file for complete search history.

(56) References Cited

U.S. PATENT DOCUMENTS

| 4,571,960 | A  | * | 2/1986  | Hursh ................. A41B 11/005 2/239 |
| 5,097,825 | A  |   | 3/1992  | Murphy |
| 6,929,617 | B2 |   | 8/2005  | McCormick et al. |
| 7,747,328 | B2 | * | 6/2010  | Chandler ................. A61N 1/32 601/15 |
| 7,862,499 | B2 | * | 1/2011  | Miller .................... A61B 17/12 600/16 |
| 2004/0215123 | A1 |   | 10/2004 | Slautterback et al. |
| 2008/0039866 | A1 | * | 2/2008  | Stetz .................... A61B 19/201 606/129 |
| 2011/0028877 | A1 |   | 2/2011  | Vollbrecht et al. |
| 2011/0230838 | A1 | * | 9/2011  | Adams ............. A61M 5/14248 604/151 |

OTHER PUBLICATIONS

International Search Report for PCT/US2015/037458.
Written Opinion for PCT/US2015/037458.

* cited by examiner

*Primary Examiner* — Brian T Gedeon
*Assistant Examiner* — Ankit Tejani
(74) *Attorney, Agent, or Firm* — Cardinal Law Group

(57) ABSTRACT

Embodiments relate to an alignment device and method. The alignment device includes a wrap and an injection device for proper alignment and insertion of a metal device.

18 Claims, 15 Drawing Sheets

ALIGNMENT WRAP

CLAIM FOR PRIORITY

This application is a continuation-in-part of application Ser. No. 14/283,354, filed May 21, 2014, the complete subject matter of which is incorporated herein by reference.

FIELD OF THE INVENTION

The present invention is in the technical field of a medical device, specifically an alignment used with a body party to inset a wire or needle. More specifically, the present invention provides alignment wraps which may be employed to position a needle electrode adjacent the tibial nerve for posterior tibial nerve stimulation used to treat a patient suffering from overactive bladder or fecal incontinence.

BACKGROUND OF THE INVENTION

Overactive bladder (OAB) and fecal incontinence (FI) are well known, non-life threatening conditions. The major symptoms of OAB include urgency, frequent urination, nocturia (interruption of sleep to urinate) and urge incontinence (unintentionally urinating followed urge to continue). FI, also called faecal incontinence, bowel incontinence and anal incontinence, is a lack of control over defecation, leading to involuntary loss of bowel contents—including flatus, liquid stool elements and mucus, or solid feces.

There are generally two types or treatment. The first type of treatment, is a stimulator implant which is a small device surgically implanted under the skin. The stimulator implant transmits electrical pulses to the sacral nerves in the lower back which stimulate the nerves that that control the bladder.

The second type of treatment is Percutaneous tibial nerve stimulation (PTNS). PTNS requires a needle be inserted a couple of inches into the area proximate or above the ankle (medial malleolus). A grounding pad is attached to the patient's foot near the heel. The needle is in turned attached to a Transcutaneous electrical nerve stimulation (TENS) which creates electrical pulses used to treat OAB and/or FI. In general, patients choose not to insert needles into themselves and are leery that the needle would be inserted in the correct location. Therefore, the patient schedules an appointment with a medical practitioner, who inserts the needle and applies the stimulation.

FIG. 1 illustrates application of such a TENS device to provide PTNS. Specifically, the TENS device includes a pulse generator 1 coupled to a first end of pair of leads 2 and 3. The other end of lead 2 is coupled to a clip 4, which is similar to an alligator clip. The clip 4 is employed to make an electrical connection between lead 2 and a needle electrode 5. The needle electrode 5 may be in the form of an acupuncture needle. As described below, the needle electrode 5 penetrates the skin at an insertion site 6. The other end of lead 3 is coupled to a surface electrode such as a patch 7 temporarily placed in contact and/or adhered to the bottom of the patient's foot 8. When in use, the pulse generator sends electrical pulses to the needle electrode 5 which pass through the tibial nerve. The patch electrode 7 and lead 3 provide a ground. The electrical pulses stimulate the tibial nerve, thus, providing therapy.

Superior results are achieved if the needle electrode 5 is inserted such that the electrode 5 resides adjacent the tibial nerve. FIG. 2 illustrates the proper injection 6 which has been marked as an X 10 on a patient's skin using a marking pen. As shown in FIG. 2, the tibial nerve of an adult human is typically located approximately 5 cm (2 inches) cephald (toward the heart) to the middle aspect of the medical malleolus (i.e., the ankle bone) 12 approximately 1 to 2 cm (¾) posterior (behind) to the tibia 14. Insertion of the needle electrode into the medial (inner) aspect of the leg at this location has proven to be efficacious when provided PTNS therapy. This is true whether the left of right leg is employed.

It would therefore be desirable to have a device that properly aligns needle for insertion at this location.

SUMMARY OF THE INVENTION

Embodiments relate to an alignment device. The alignment includes a wrap; and an injection device for proper alignment and insertion of a metal device such as a needle electrode, adjacent to the tibial nerve. More specifically, embodiments related to an alignment device including a wrap adapted to be position on the foot and lower leg of a patient to be treated, the wrap having a first opening adapted to be positioned over an injection site proximate the tibial nerve of the patient; and (b) means for indexing the wrap so that the first opening is positioned over the injection site.

Other embodiments relate to an alignment device for use with a body for treatment of medical conditions such as OAB and/or FI. The alignment device includes a wrap having a first end and a second end for use in contact with a portion of the body; and a securement device for securing the first end to the second end. The alignment device further defines a tube having a first open end in contact with the portion of the human body, the alignment device providing proper alignment and insertion of a metal device such as a needle electrode.

Yet other embodiments relate to a method for inserting a metal device such as a needle electrode into a portion of a human body using an alignment device. The alignment device includes a wrap; and an injection device for proper alignment and insertion of the metal device. The method includes positioning the wrap on the portion of the human body; and slowly twisting and inserting the metal device.

The foregoing and other features and advantages of the invention will become further apparent from the following detailed description of the presently preferred embodiment, read in conjunction with the accompanying drawings. The drawings are not to scale. The detailed description and drawings are merely illustrative of the invention rather than limiting, the scope of the invention being defined by the appended claims and equivalents thereof.

BRIEF DESCRIPTION OF THE DRAWINGS

Throughout the various figures, like reference numbers refer to like elements.

DETAILED DESCRIPTION OF PRESENTLY PREFERRED EMBODIMENTS

Figure 1:
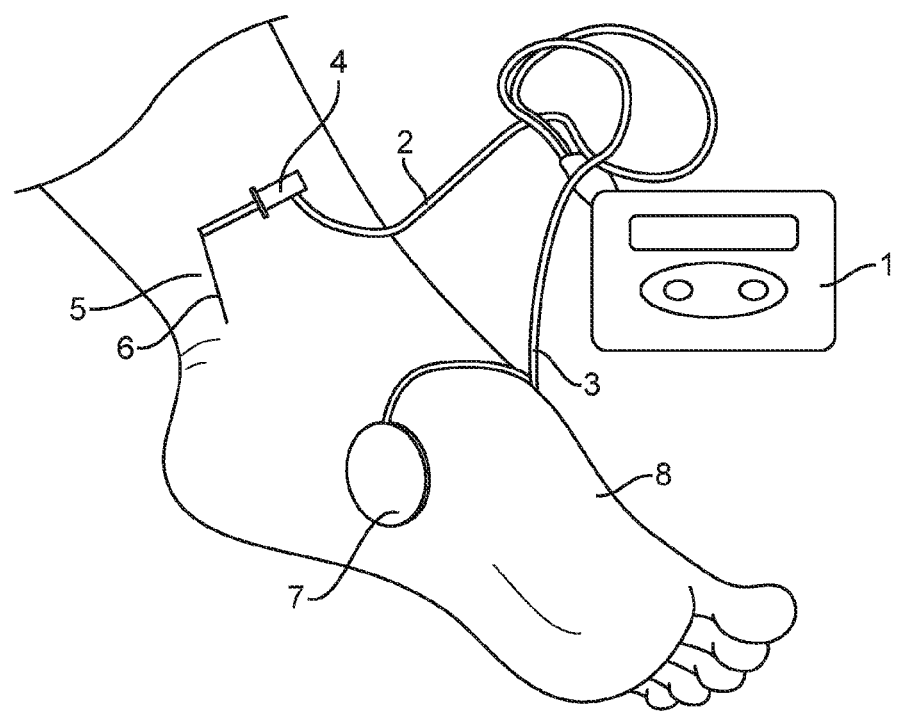
FIG. 1 illustrates a prior art TENS system coupled to a patient's lower leg and foot.
Figure 2:
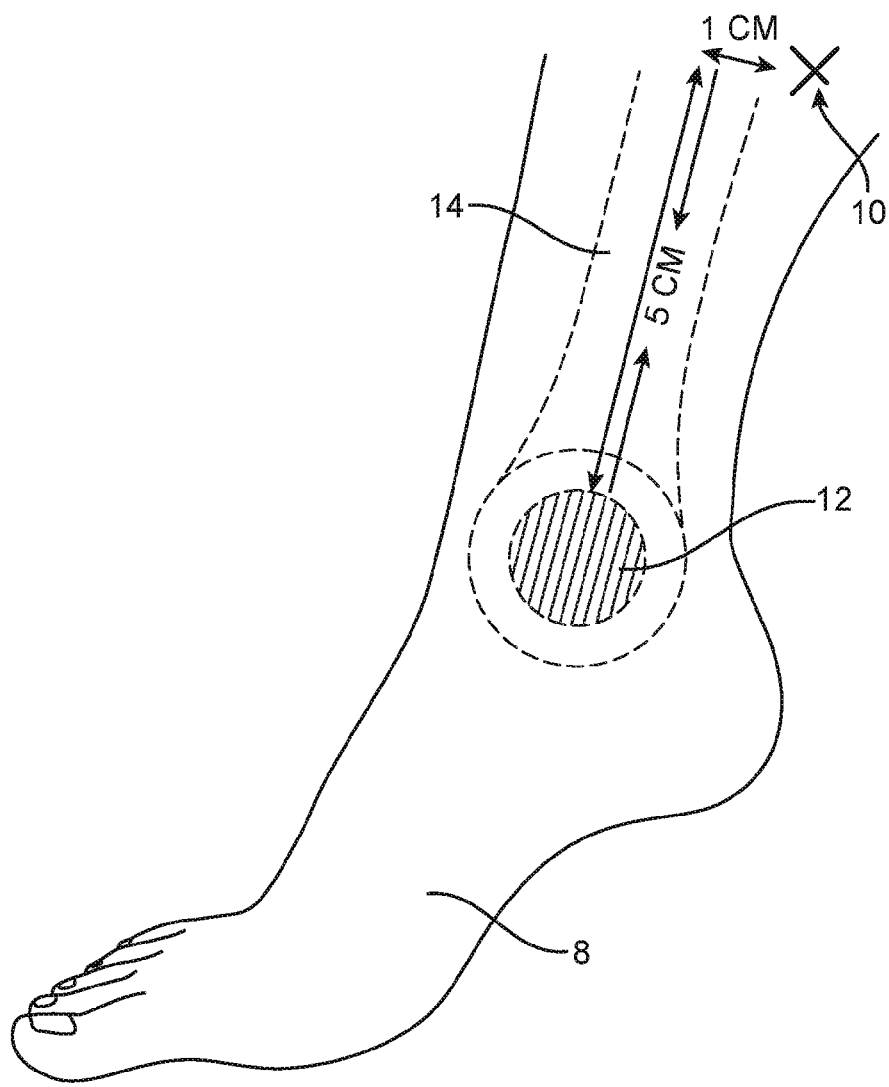
FIG. 2 illustrates an ankle of a patient and illustrates a method for determining a suitable injection cite for a needle electrode when using a TENS system to perform PTNS.

Embodiments of the present invention relate to an alignment device 10 used with a body part. FIGS. 1 and 2 illustrate a foot 8 having an insertion site 6 proximate ankles. Insertion site 6 is shown as being approximately 5 cm (2 inches) cephald (toward the heart) to the middle aspect of the medial malleolus (ankle bone) 12 and approximately 1 to 2 cm (¾ inch) posterior (behind) to the tibia 14. In the past, medical practitioners have measured to locate the insertion site 6 and then marked the insertion site on the skin with a marker. In FIG. 2, such a marking 10 is shown in the form of an "X". The insertion site is then disinfected using any known topical disinfectant and a needle electrode (see, e.g. 5 in FIG. 1) is then inserted through the skin at injection site so it is proximate to the tibial nerve.

Figure 3:
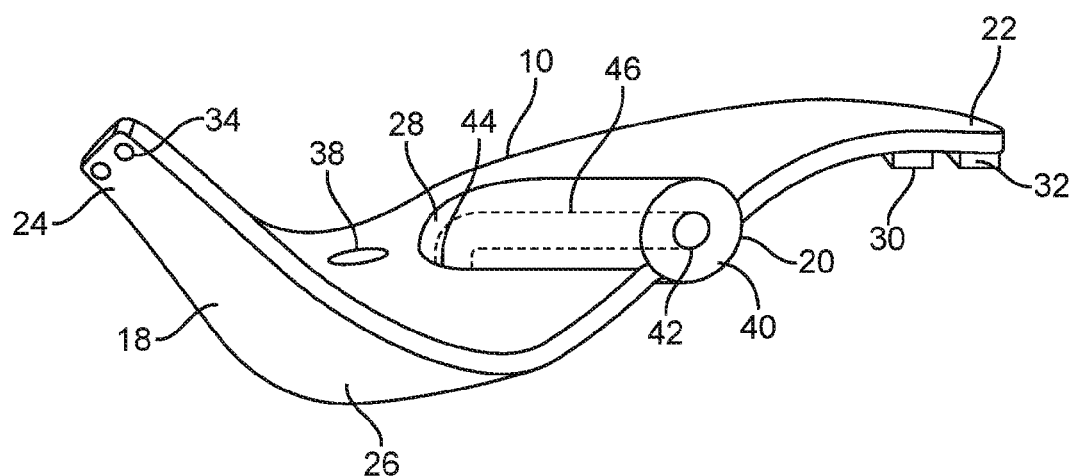
FIG. 3 illustrates a first view of the alignment device used with the ankle of FIG. 1 in accordance with the present invention.
Figure 4:
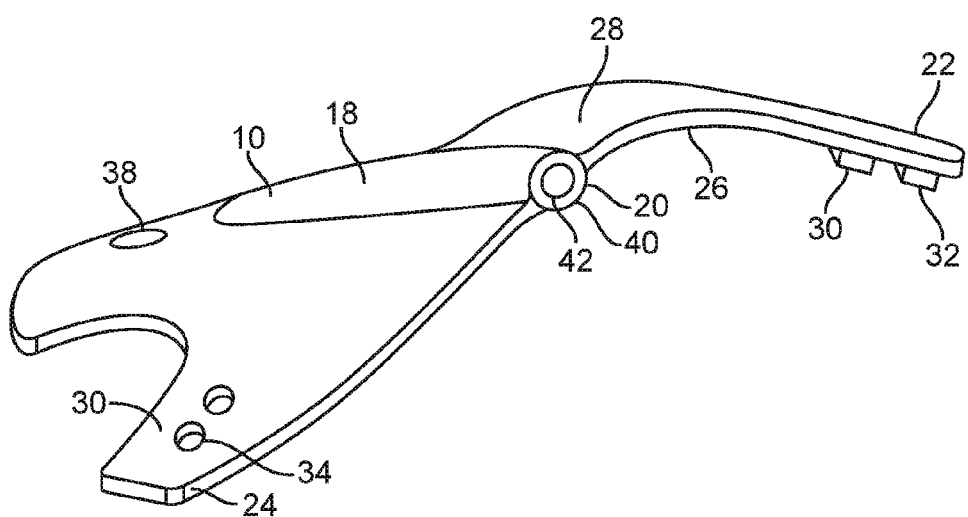
FIG. 4 illustrates a second view of the alignment device of FIG. 2.

The alignment device 10 illustrated in FIGS. 3-4 may be employed to assist a patient or other person in placing a needle electrode proximate the tibial nerve. The alignment device includes a wrap 18 and an injection device 20 used for proper alignment and insertion of a metal device such as a needle electrode for treatment of medical conditions such as OAB and fecal incontinence.

In at least one embodiment the wrap 18 is a single unit having first end 22 and a second end 24. Wrap 18 further includes a first side 26 and a second side 28 opposite the first side 26, where the second side 28 is adapted to be placed against skin of the patient's foot 12. Wrap 10 further includes a securement device 30 for securing the first end 22 and second end 24. In the embodiment illustrated in FIGS. 3-4, securement device 30 includes one or more male snaps 32 located at first end 22 adapted to frictionally fit female snaps 34 located at second end 24.

In at least one embodiment, while snaps 32 and 34 are contemplated, other arrangements including hook and loops, hook and eyes, ties, snaps, buckles and the likes are contemplated. Furthermore, the wrap 10 is a single unit, although other embodiments such as two or more separate units removably secured together are contemplated as provide below.

FIGS. 3-4 depict one embodiment of the injection device 20. In the illustrated embodiment, injection device 20 comprises a tube 40 having a first end 42, a second end 44 and a bore 46 extending between first end 42 and a second end 44. As illustrated, second end 44 is adapted to be positioned at the insertion site proximate the ankle 16. More specifically, the wrap is indexed to the foot as it is placed about the foot to ensure the opening of the bore 46 through the second end 44 is properly aligned with the injection site marking 10.

Indexing of the bore 46 with the injection site 1 can be accomplished in several ways. For example, the injection site can be marked on the skin using a suitable pen or other marking device. The tube can then be visually aligned with the mark at the injection site by looking down the bore while securing the wrap in place. Alternatively, the wrap can be sized and indexed with structures of the foot, such as the heel or ankle bone such as fitting the wrap over the foot ensures the bore of the tube will be aligned with the injection site.

In one embodiment, the injection device 20 comprises a spring loaded tube, adapted to slowly twist and insert a metal device such as a needle electrode upon insertion. Additionally, the injection device 20 may comprise a guide tube used to insert the metal device by applying a mechanical or manual force to the guide tube and/or the metal device. Alternatively, the injection device may comprise a pneumatic device, a hydraulic device and the like and/or contain a plurality of metal devices, where the insertion depth of the metal devices is selectable.

In one or more embodiments of the present invention, the metal device is selected from a wire, a needle, an electrically conductive metal device and the like. Further the metal device is adapted to be electrically connectable to an electrical device, transmitting electrical pulses from the electrical device to the patient's foot.

In one or more embodiments, the wrap 10 may be a single unit made of a material selected from the group comprising an elastic gauze, elastic adhesive material, cotton, wool, nylon, and neoprene. In at least one embodiment, the wrap 10 defines a hole 38 which is adapted to receive the heel 14, such that the second end 44 is positioned proximate the ankle 16. Alternatively, the wrap 10 may be made up of two or more pieces which are made up of gel pads or air bladders, placed on opposite sides of the patient's ankle and secured in place by straps, belts, tape and the like.

Figure 5:
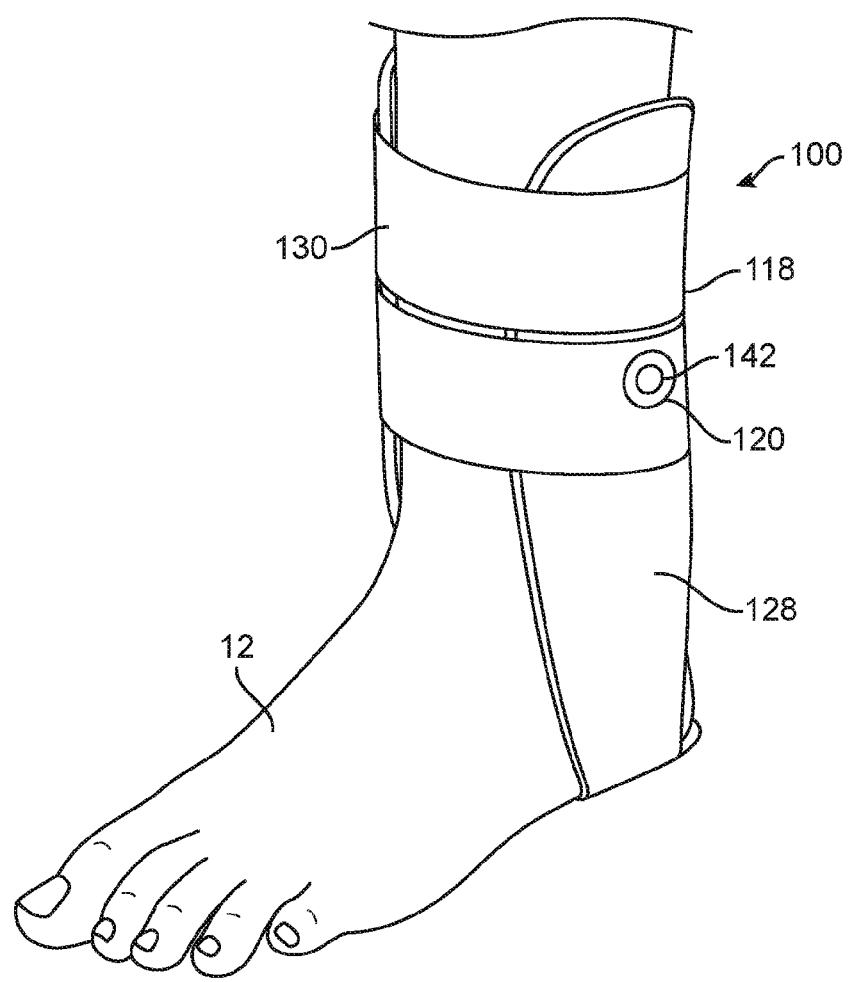
FIG. 5 illustrates a first view of an alignment device in accordance with another embodiment used with an ankle similar to that of FIG. 1.
Figure 6:
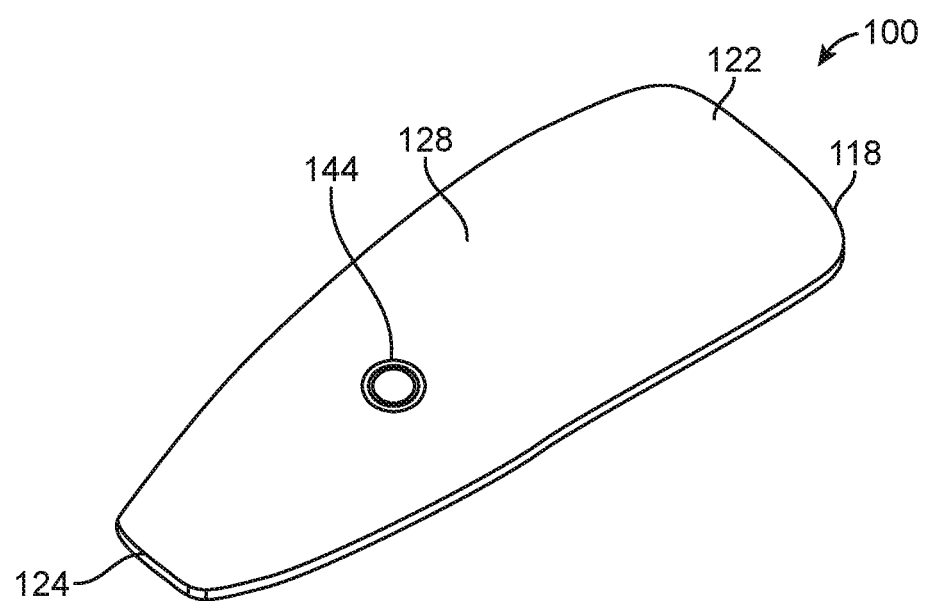
FIG. 6 illustrates a second view of the alignment device of FIG. 4.

FIGS. 5-6 illustrate views of an alignment device 100 used with the ankle of FIG. 1 in accordance with another embodiment. In this embodiment the wrap 118 is a unit having first end 122 and a second end 124. Wrap 118 further includes a first side 126 and a second side 128 opposite the first side 126, where the second side 128 is adapted to be placed against skin of the patient's foot 12. Wrap 118 further includes a securement device 130 for securing the wrap 118. In the embodiment illustrated in FIGS. 5-6, securement device 130 includes one or more straps located proximate first end 122 adapted to couple to each other or the wrap 118 using a hook and loop arrangement for example.

FIGS. 5-6 depict one embodiment of the injection device 120. In the illustrated embodiment, injection device 120 comprises a tube having a first end 142, a second end 144 and a bore extending between first end 142 and a second end 144. As illustrated, second end 144 is adapted to be positioned at the insertion site proximate the ankle 16. Indexing the bore with the injection site 15 can be achieved by first marking the skin at the injection site and then looking down the bore to ensure the bore is aligned with the injection site as the securement device 130 is employed to secure wrap 18 in place. Alternatively, the wrap 118 may include a pocket 129 that catches the bottom of the heel to ensure proper front-to-back positioning such that when the tops of the two sides 128 and 130 are at the same height, the bore will reside over the injection site.

In one embodiment, the injection device 120 comprises a spring loaded tube, adapted to slowly twist and insert a metal device upon insertion. Additionally, the injection device 120 may comprise a guide tube used to insert the metal device by applying a mechanical or manual force to the guide tube and/or the metal device. Alternatively, the injection device 120 may comprise a pneumatic device, a hydraulic device and the like and/or contain a plurality of metal devices, where the insertion depth of the metal devices is selectable.

In one or more embodiments, the wrap 118 may be of a single unit of a material selected from a group comprising plastic, carbon fiber or any other suitable hard material while the securement device 130 may be of a material selected from the group comprising an elastic gauze, elastic adhesive material, cotton, wool, nylon, neoprene, ties, shoe strings, adjustable straps, rubber straps and the like. In at least one embodiment, the wrap 118 defines a hole which is adapted to receive the heel, such that the second end 144 is positioned proximate the ankle 16. Alternatively, the wrap 118 may be made up of two or more pieces which may include gel pads or air bladders, placed on opposite sides of the patient's ankle and secured in place by straps, belts, tape and the like.

Figure 7:
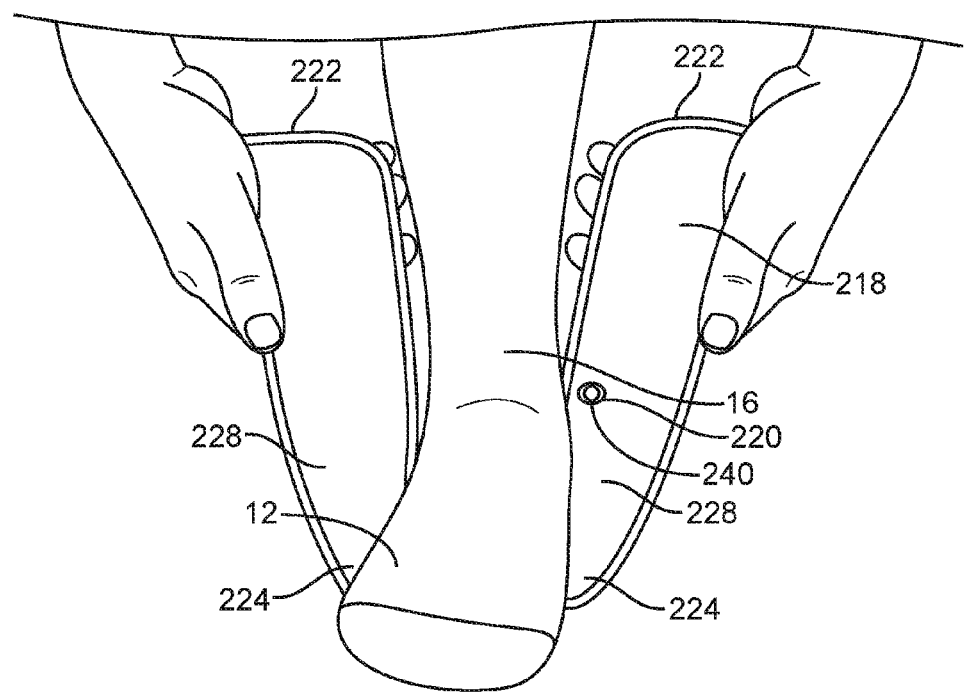
FIG. 7 illustrates a first view of an alignment device in accordance with still another embodiment used with an ankle similar to that of FIG. 1.
Figure 8:
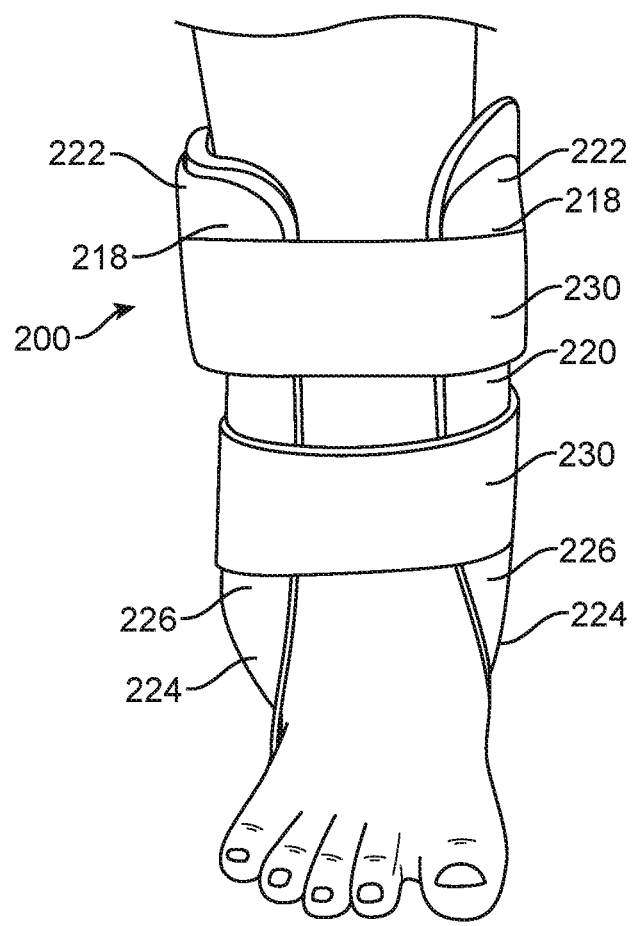
FIG. 8 illustrates a second view of the alignment device of FIG. 6 used with the ankle of FIG. 1.

FIGS. 7-8 illustrate views of an alignment device 200 used with the ankle of FIGS. 1 and 2 in accordance with another embodiment. In this embodiment the wrap 218 includes two units positionable on either side of angle 12, each unit of wrap 218 having first end 222 and a second end 224. Each unit of wrap 218 further includes a first side 226 and a second side 228 opposite the first side 226, where the second side 228 is adapted to be placed against skin of the patient's foot 12. Wrap 218 further includes a securement device 230 for securing the wrap 218.

In the embodiment illustrated in FIGS. 7-8, securement device 230 includes one or more straps located between first end 222 and second end 224 adapted to couple to each other or the wrap 218 using a hook and loop arrangement although other means are contemplated.

FIGS. 7-8 depict one embodiment of the injection device 220 located on each of the units, positionable on both sides of the ankle 12. In the illustrated embodiment, each injection device 220 comprises a tube having a first end 242, a second end 244 and a bore extending between first end 242 and a second end 244. As illustrated, each second end 244 is adapted to be positioned at the insertion site proximate the ankle 16.

In one embodiment, the injection device 220 comprises a spring loaded tube, adapted to slowly twist and insert a metal device upon insertion. Additionally, the injection device 220 may comprise a guide tube used to insert the metal device by applying a mechanical or manual force to the guide tube and/or the metal device. Alternatively, the injection device 220 may comprise a pneumatic device, a hydraulic device and the like and/or contain a plurality of metal devices, where the insertion depth of the metal devices is selectable.

In one or more embodiments, the wrap 218 may of a material selected from a group comprising plastic, carbon fiber or any other suitable hard material while the securement device 230 may be of a material selected from the group comprising an elastic gauze, elastic adhesive material, cotton, wool, nylon, neoprene, ties, shoe strings, adjustable straps, rubber straps and the like. When forming the wrap 218 out of plastic, carbon fiber or other suitable materials, structures may be molded into the wrap which cooperate with the ankle bone, heel or other structures of the foot and lower leg to ensure the bore is aligned (indexed) with the injection site. In fact, the wrap can be molded in a customized fashion for use by a specific patient to ensure the bore is properly indexed with the injection site. Alternatively, the injection site may be marked on the skin and the bore visually aligned with the marking.

Figure 9:
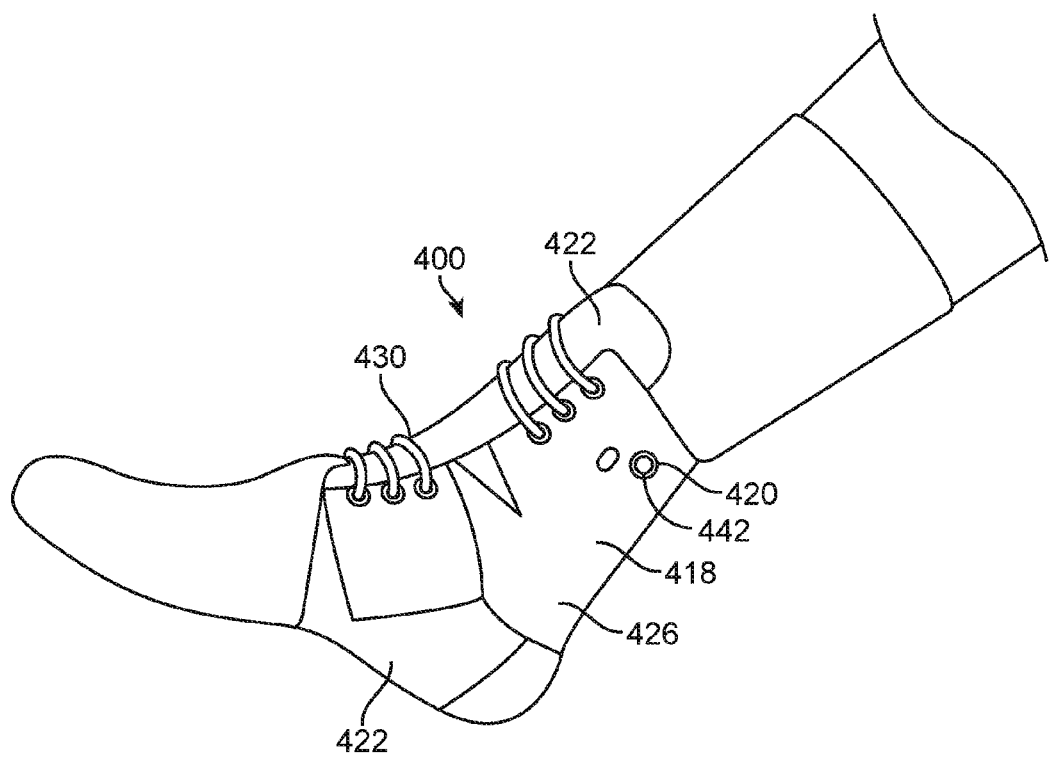
FIG. 9 illustrates a view of an alignment device in accordance with another embodiment used with an ankle similar to that of FIG. 1.

FIG. 9 illustrates a view of an alignment device 300 used with the ankle of FIGS. 1 and 2 in accordance with another embodiment. In this embodiment the wrap 318 is a unit having first end 322 and a second end 324. Wrap 318 further includes a first side 326 and a second side opposite the first side 326, where the second side is adapted to be placed against skin of the patient's foot 12. Wrap 318 further includes a securement device 330 for securing the wrap 318. In the embodiment illustrated in FIG. 9, securement device 330 includes one or more ties or shoe strings extending from first end 322 towards second end 324 and is adapted to coupled or tied to each other.

FIG. 9 depicts one embodiment of the injection device 320. In the illustrated embodiment, injection device 320 comprises a tube having a first end 342, a second end and a bore extending between first end 342 and second end. As illustrated, the second end is adapted to be positioned at the insertion site proximate the ankle 16.

One skilled in the art will appreciate that the wrap 318 of FIG. 9 is essentially a boot with separate openings for the front of the foot, the heel and the leg. These openings index the boot so that when it is placed on the foot, as illustrated in FIG. 8, the injection device 320 is properly indexed to the injection site.

In one embodiment, the injection device 320 comprises a spring loaded tube, adapted to slowly twist and insert a metal device upon insertion. Additionally, the injection device 320 may comprise a guide tube used to insert the metal device by applying a mechanical or manual force to the guide tube and/or the metal device. Alternatively, the injection device 320 may comprise a pneumatic device, a hydraulic device and the like and/or contain a plurality of metal devices, where the insertion depth of the metal devices is selectable.

In one or more embodiments, the wrap 318 may be of a single unit of a material selected from a group comprising plastic, carbon fiber or any other suitable hard material while the securement device 330 may be of a material selected from the group comprising an elastic gauze, elastic adhesive material, cotton, wool, nylon, neoprene, ties, shoe strings, adjustable straps, rubber straps and the like. In at least one embodiment, the wrap 318 receives the heel, such that the second end is positioned proximate the ankle 16.

Figure 10:
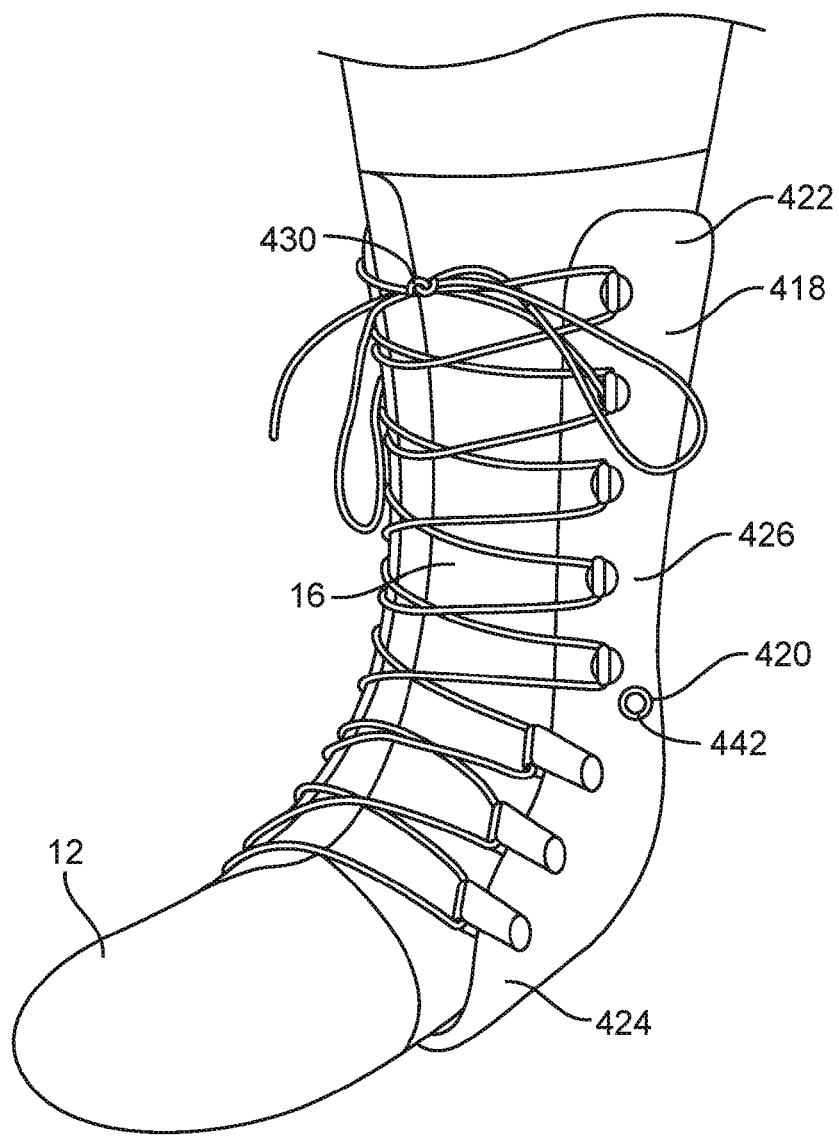
FIG. 10 illustrates a view of an alignment device in accordance with another embodiment used with an ankle similar to that of FIG. 1.

FIG. 10 illustrates a view of an alignment device 400 used with the ankle of FIGS. 1 and 2 in accordance with another embodiment. In this embodiment the wrap 418 is a unit having first end 422 and a second end 424. Wrap 418 further includes a first side 426 and a second side opposite the first side 426, where the second side is adapted to be placed against skin of the patient's foot 12. Wrap 418 further includes a securement device 430 for securing the wrap 418. In the embodiment illustrated in FIG. 10, securement device 430 includes one or more straps ties or shoe strings extending from first end 422 towards second end 424 and is adapted to coupled or tied to each other.

FIG. 10 depicts one embodiment of the injection device 418. In the illustrated embodiment, injection device 420 comprises a tube having a first end 442, a second end and a bore extending between first end 442 and second end. As illustrated, the second end is adapted to be positioned at the insertion site proximate the ankle 16.

Indexing of the wrap 418 and injection device 420 of FIG. 10 relative to the injection site is achieved in a fashion similar to that described above with reference to FIG. 8. In the embodiment of FIG. 10, similar holes are provided through which front of the foot and leg extend. Rather than previously a hole for the heel, the wrap is structured to conform to the shape of the heel and ankle. As such, the heel and ankle portions of the boot and the holes for the front of the foot and leg cooperate with the wearer's foot and leg to index (align) the bore of tube 420 with the injection site.

In one embodiment, the injection device 420 comprises a spring loaded tube, adapted to slowly twist and insert a metal device upon insertion. Additionally, the injection device 420 may comprise a guide tube used to insert the metal device by applying a mechanical or manual force to the guide tube and/or the metal device. Alternatively, the injection device 420 may comprise a pneumatic device, a hydraulic device and the like and/or contain a plurality of metal devices, where the insertion depth of the metal devices is selectable.

In one or more embodiments, the wrap 418 may be of a single unit of a material selected from a group comprising plastic, carbon fiber or any other suitable hard material while the securement device 430 may be of a material selected from the group comprising an elastic gauze, elastic adhesive material, cotton, wool, nylon, neoprene, ties, shoe strings, adjustable straps, rubber straps and the like. In at least one embodiment, the wrap 418 receives the heel, such that the second end is positioned proximate the ankle 16.

Figure 11:
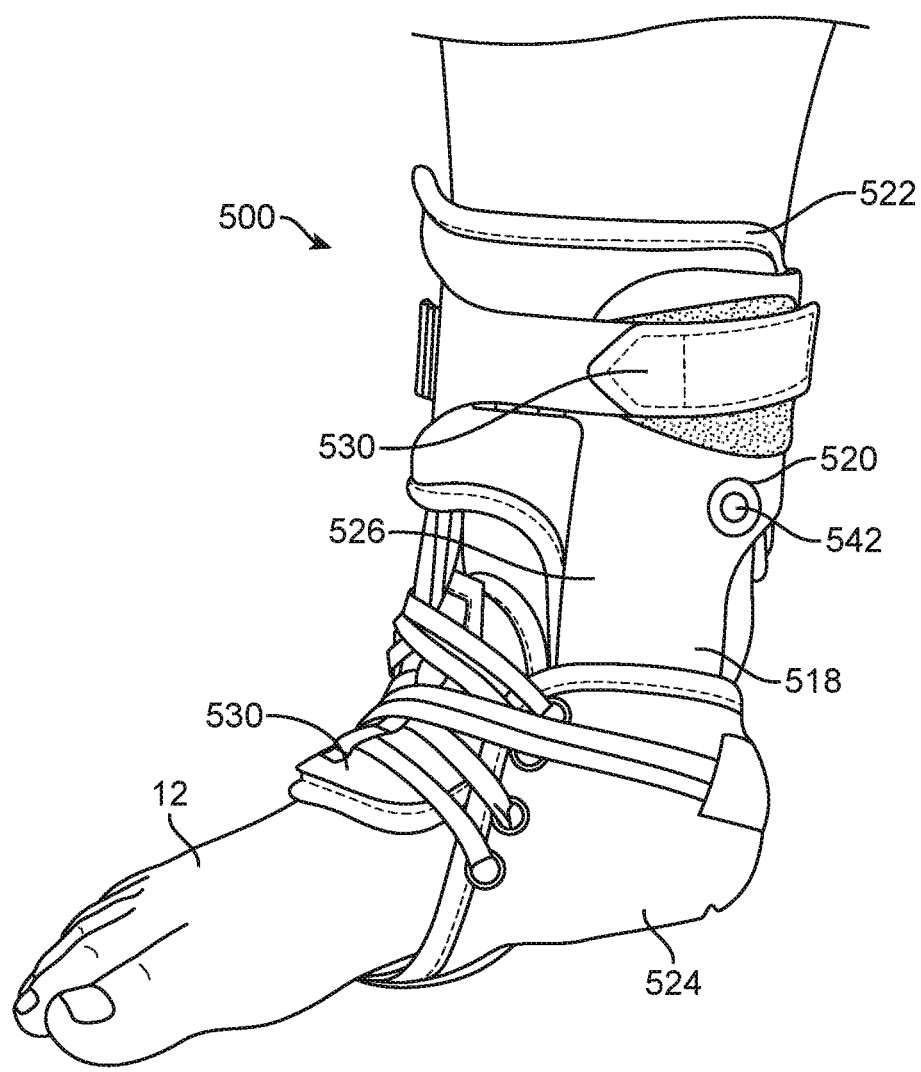
FIG. 11 illustrates a view of an alignment device in accordance with another embodiment used with an ankle similar to that of FIG. 1.

FIG. 11 illustrates a view of an alignment device 500 in accordance with another embodiment used with an ankle similar to that of FIG. 3. In this embodiment the wrap 518 is a unit having first end 522 and a second end 524. Wrap 518 further includes a first side 526 and a second side opposite the first side 526, where the second side is adapted to be placed against skin of the patient's foot 12. Wrap 518 further includes a securement device 530 for securing the wrap 518. In the embodiment illustrated in FIG. 11, securement device 530 includes one or more Velcro™ straps.

FIG. 11 depicts one embodiment of the injection device 520. In the illustrated embodiment, injection device 520 comprises a tube having a first end 542, a second end and a bore extending between first end 542 and second end. As illustrated, the second end is adapted to be positioned at the insertion site proximate the ankle 16.

In one embodiment, the injection device 520 comprises a spring loaded tube, adapted to slowly twist and insert a metal device upon insertion. Additionally, the injection device 520 may comprise a guide tube used to insert the metal device by applying a mechanical or manual force to the guide tube and/or the metal device. Alternatively, the injection device 520 may comprise a pneumatic device, a hydraulic device and the like and/or contain a plurality of metal devices, where the insertion depth of the metal devices is selectable.

In one or more embodiments, the wrap 518 may be of a single unit of a material selected from a group comprising plastic, carbon fiber or any other suitable hard material while the securement device 530 may be of a material selected from the group comprising an elastic gauze, elastic adhesive material, cotton, wool, nylon, neoprene, ties, shoe strings, adjustable straps, rubber straps and the like. In at least one embodiment, the wrap 518 receives the heel, such that the second end is positioned proximate the ankle 16. Indexing of the tube with the injection site is achieved in this embodiment in the same way described above with reference to FIG. 10.

Figure 12:
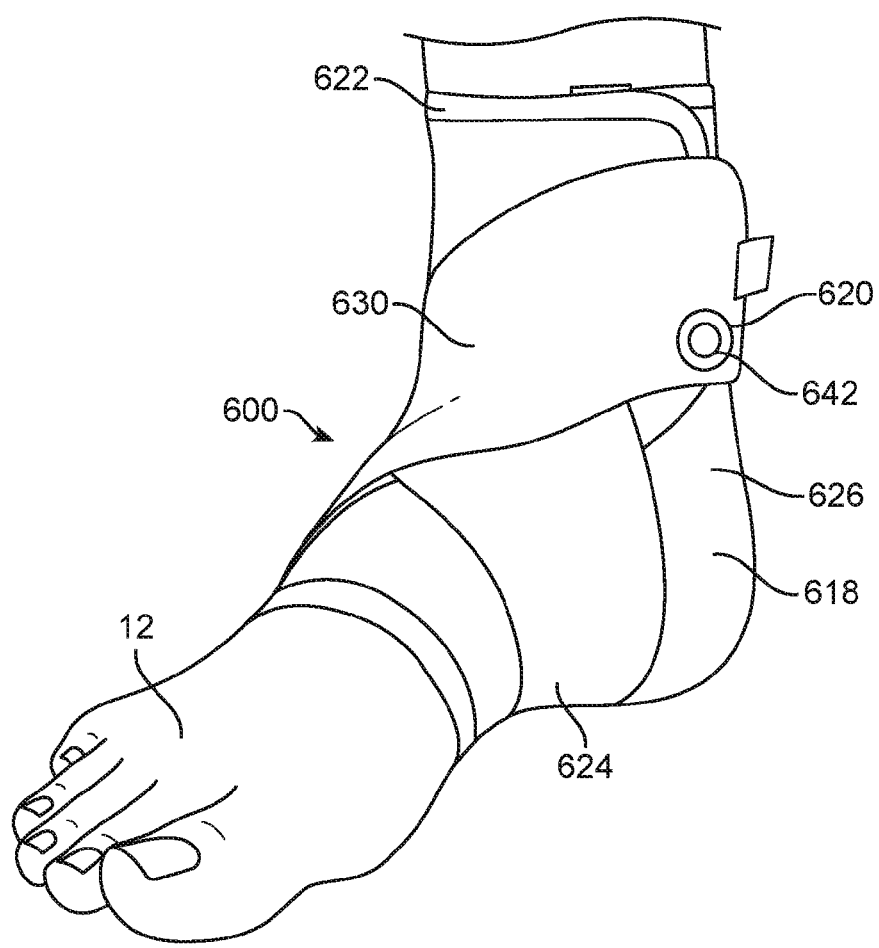
FIG. 12 illustrates a view of an alignment device in accordance with another embodiment used with an ankle similar to that of FIG. 1.

FIG. 12 illustrates a view of an alignment device 600 in accordance with another embodiment used with an ankle similar to that of FIG. 3. In this embodiment the wrap 618 is a unit having first end 622 and a second end 624. Wrap 618 further includes a first side 626 and a second side opposite the first side 626, where the second side is adapted to be placed against skin of the patient's foot 12. Wrap 618 further includes a securement device 630 for securing the wrap 618. In the embodiment illustrated in FIG. 12, securement device 630 includes one or more Velcro™ straps.

FIG. 12 depicts one embodiment of the injection device 620. In the illustrated embodiment, injection device 620 comprises a tube having a first end 642, a second end and a bore extending between first end 642 and second end. As illustrated, the second end is adapted to be positioned at the insertion site proximate the ankle 16.

In one embodiment, the injection device 620 comprises a spring loaded tube, adapted to slowly twist and insert a metal device upon insertion. Additionally, the injection device 620 may comprise a guide tube used to insert the metal device by applying a mechanical or manual force to the guide tube and/or the metal device. Alternatively, the injection device 620 may comprise a pneumatic device, a hydraulic device and the like and/or contain a plurality of metal devices, where the insertion depth of the metal devices is selectable.

In one or more embodiments, the wrap 618 may be of a single unit of a material selected from a group comprising plastic, carbon fiber or any other suitable hard material while the securement device 630 may be of a material selected from the group comprising an elastic gauze, elastic adhesive material, cotton, wool, nylon, neoprene, ties, shoe strings, adjustable straps, rubber straps and the like. In at least one embodiment, the wrap 618 receives the heel, such that the second end is positioned proximate the ankle 16.

Figure 13:
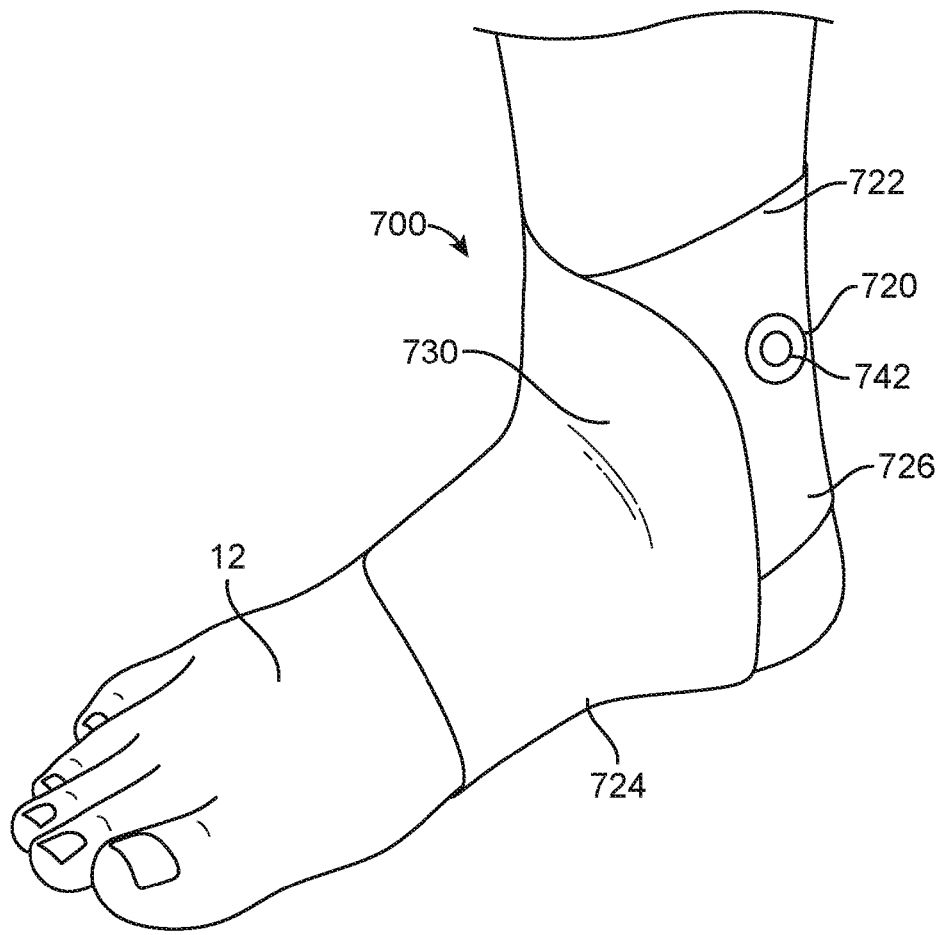
FIG. 13 illustrates a view of an alignment device in accordance with another embodiment used with an ankle similar to that of FIG. 1.

FIG. 13 illustrates a view of an alignment device 700 in accordance with another embodiment used with an ankle similar to that of FIG. 3. In this embodiment the wrap 718 is a unit having first end 722 and a second end 724. Wrap 718 further includes a first side 726 and a second side opposite the first side 726, where the second side is adapted to be placed against skin of the patient's foot 12. Wrap 718 further includes a securement device 730 for securing the wrap 718. In the embodiment illustrated in FIG. 13, securement device 730 includes one or more Velcro™ straps.

FIG. 13 depicts one embodiment of the injection device 720. In the illustrated embodiment, injection device 720 comprises a tube having a first end 742, a second end and a bore extending between first end 742 and second end. As illustrated, the second end is adapted to be positioned at the insertion site proximate the ankle 16.

In one embodiment, the injection device 720 comprises a spring loaded tube, adapted to slowly twist and insert a metal device upon insertion. Additionally, the injection device 720 may comprise a guide tube used to insert the metal device by applying a mechanical or manual force to the guide tube and/or the metal device. Alternatively, the injection device 720 may comprise a pneumatic device, a hydraulic device and the like and/or contain a plurality of metal devices, where the insertion depth of the metal devices is selectable.

In one or more embodiments, the wrap 718 may be of a single unit of a material selected from a group comprising plastic, carbon fiber or any other suitable hard material while the securement device 730 may be of a material selected from the group comprising an elastic gauze, elastic adhesive material, cotton, wool, nylon, neoprene, ties, shoe strings, adjustable straps, rubber straps and the like. In at least one embodiment, the wrap 718 receives the heel, such that the second end is positioned proximate the ankle 16. In both the embodiment shown in FIG. 12 and the embodiment shown in FIG. 13, alignment of the injection device with the injection site is achieved by first marking the injection site and then viewing the marking through the tube.

Figure 14:
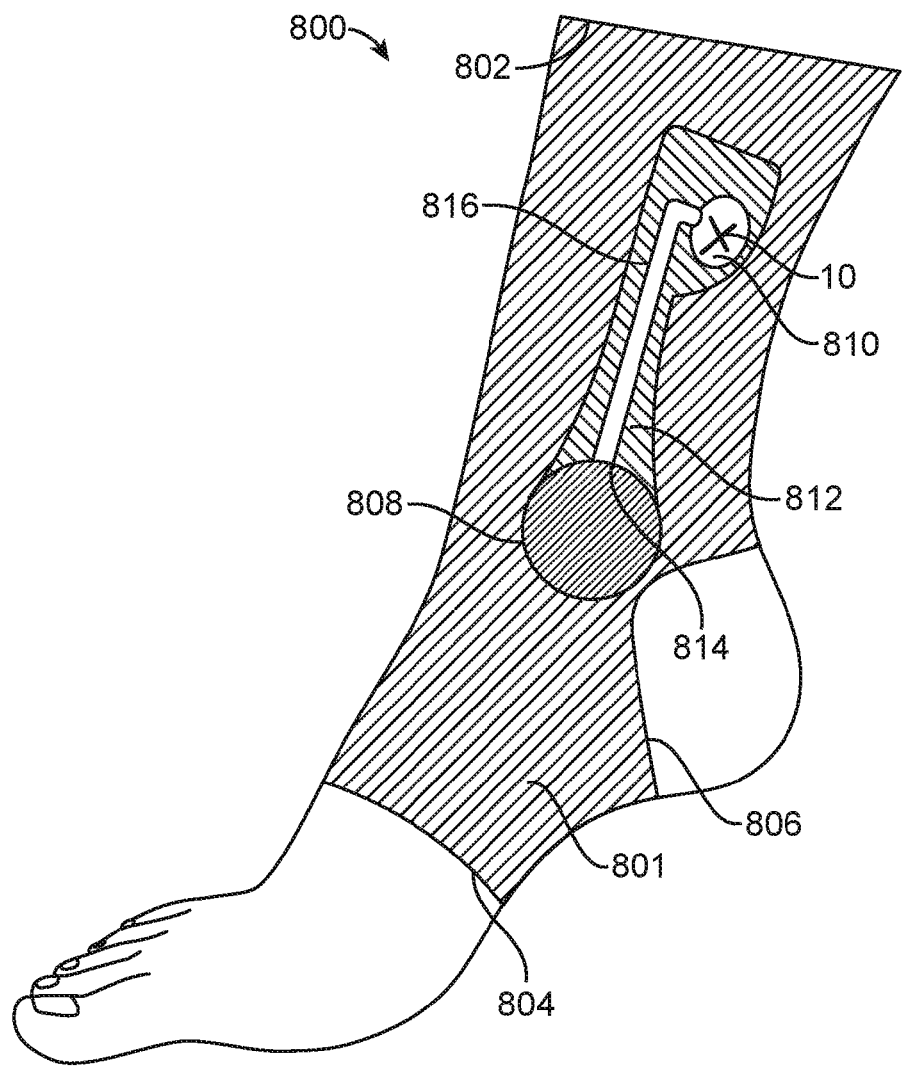
FIG. 14 illustrates an alignment device in accordance with another embodiment similar to the alignment device of FIG. 1.

FIG. 14 shows an alignment device 800 comprising a sock-like wrap having a top opening 802 for the leg, a bottom opening 804 for the front of the foot, a heel opening 806, an ankle opening 808 and an opening 810 over the injection site which is marked on the skin with an "X" labeled 10. Also shown in FIG. 14 is a reinforced wedge 812 extending from the ankle opening 802 to and surrounding the opening 810 over the injection site. The wedge 812 has a curved face 814 which engages the ankle of the patient. Also shown is a marking 816 on the sock-like wrap 811. The marking 816 extends from a point proximate the ankle opening 808 to a point proximate opening 810. The various openings, together with the wedge 812 and the marking 816 assist in indexing and aligning the sock-like wrap 801 so that the opening 810 resides over the injection site.

Figure 15:
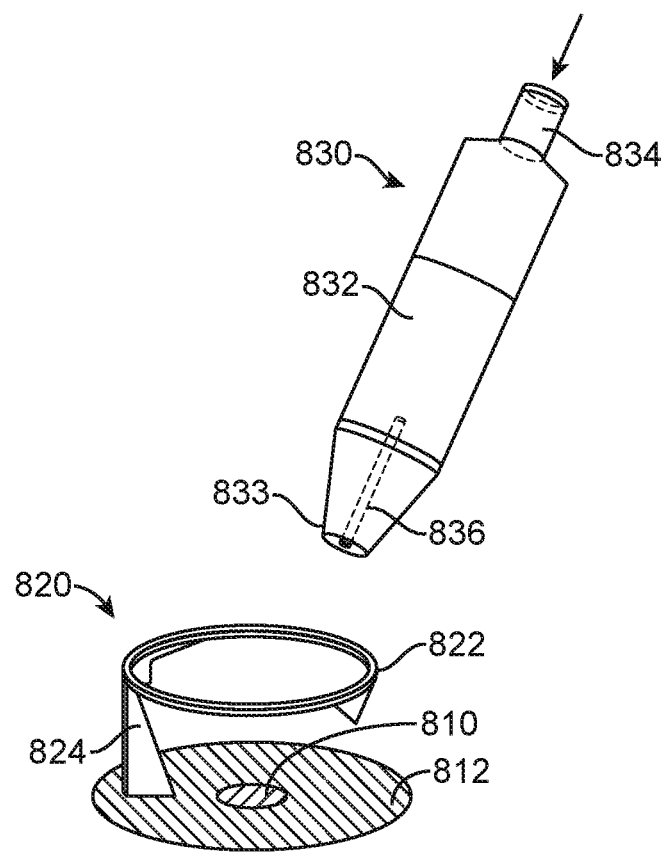
FIG. 15 shows a needle drive and an optional chimney guide.

FIG. 15 shows the portion of wedge 812 surrounding opening 810. Coupled to the wedge 812 is an optional chimney guide 820 having an elevated ring 822 and a stem 824. The bottom of the stem 824 is adapted to couple the guide 820 to the wedge 812. Such coupling can occur in any of a variety of ways. The coupling means employed permits the chimney guide to be quickly and easily coupled to and decoupled from the wedge 812, or alternatively, the sock-like wrap 801. Alternatively, a chimney guide may be integrally formed with or permanently affixed to the wrap 801 (or any of the other wraps discussed above) or to the wedge 812. Also shown in FIG. 15 is a needle driver 830. The needle driver 830 has a housing 832, a reciprocating plunger 834 and a needle channel 836. The tip 833 of the housing 832 is tapered. When used with the optional chimney guide 820, a needle electrode (such as needle electrode 5) is inserted into the needle channel 826. The tip 833 of housing 832 is then mated with the ring 822 of the optional guide so that the opening of the needle channel 836 is positioned over the injection site which may or may not be pre-marked on the skin of the patient with an "X". When the needle driver 830 is so positioned, the plunger 834 is pushed into the housing 832 and forces the needle electrode 5 out of the housing and through the skin so that the tip of the needle electrode 5 resides in the injection site adjacent the tibial nerve. The housing 832, plunger 834, needle electrode 5 and guide are all adapted in terms of size and shape to ensure not only that the tip of the needle electrode 5 is adjacent the tibial nerve, but also that the shaft of the needle electrode 5 extends out of the skin so that the shaft of the needle electrode 5 can be easily coupled to clip 4 and easily grasped for removal once a treatment session has been completed. Of course, when the optional chimney guide is not employed, the needle driver 830 should be adapted to achieve similar results with respect to placement of the needle electrode 5 when the tip 833 of house 832 is brought into contact with the injection site and the plunger 834 is depressed.

FIGS. 3 and 4 illustrates that the injection device 20 is positioned such that the metal device is inserted into ankle 12 at about a 45 degree angle to a plane defined by ankle 12. However embodiments are contemplated in which the metal device is inserted at different angles, for example, in the embodiments illustrated in FIGS. 5-15, the injection devices 120/220/320 and 420 are positioned such that the metal device is inserted at about a 90 degree angle to a plane defined by ankle 12. However, that angle could range from about 15 degrees to about 165 degrees to the plane defined by ankle 12 or more specifically between about 30 degrees and 90 degrees to the plane defined by ankle 12.

FIG. 16 illustrates one or more embodiments relating to a method generally designate 900, for inserting a metal device into a portion of a human body (an ankle for example) using any of the alignment devices as provided above. The method 900 comprises positioning the wrap around the patient's foot 12 and the second side is adapted to be placed against skin of the patient's ankle 12 and injection device 20 is positioned adjacent ankle, block 910.

The alignment device 10 is then secured using the securement device, block 912. Method 900 further comprises slowly twisting and inserting the metal device into the patient, block 914. The metal device is connected to an electrical device, block 916. Electrical pulses are transmitted to the patient's nerves from the electrical device and the metal device, block 918. While the embodiments of the invention disclosed herein are presently considered to be preferred, various changes and modifications can be made without departing from the spirit and scope of the invention.

The scope of the invention is indicated in the appended claims, and all changes that come within the meaning and range of equivalents are intended to be embraced therein.

The invention claimed is:

1. An alignment device comprising:
   (a) a wrap adapted to be positioned on the foot and lower leg of a patient to be treated, the wrap having a first opening adapted to be positioned over an injection site proximate the tibial nerve of the patient;
   (b) means for indexing the wrap so that the first opening is positioned over the injection site; and
   (c) a chimney guide comprising an elevated ring and a stem.

2. The alignment device of claim 1 further wherein the means for indexing the wrap comprises a reinforcing wedge extending between a curved face adapted to engage the ankle of the patient and the injection site, the reinforcing wedge having a second opening adapted to be positioned over the injection site and aligned with the first opening of the wrap.

3. The alignment device of claim 2 wherein the bottom of the stem is adapted to be coupled to the chimney guide to the wedge proximate the second opening.

4. The alignment device of claim 2 wherein the chimney guide is permanently affixed to a reinforcing wedge proximate the second opening.

5. The alignment device of claim 2 further comprising a needle driver having a housing terminating in a tip, a reciprocating plunger, and a needle channel, and wherein the tip of the needle driver housing is adapted to mate with the first opening and the second opening to position the needle channel in alignment with the injection site.

6. The alignment device of claim 2 further comprising a needle driver having a housing terminating in a tip, a reciprocating plunger, and a needle channel, and wherein the tip of the needle driver is adapted to pass through the elevated ring of the chimney guide and mate with the first opening and the second opening to align the needle channel over the injection site.

7. The alignment device of claim 2 wherein the reinforcing wedge is integrally formed with the wrap.

8. The alignment device of claim 1 wherein the means for aligning the wrap comprises at least one alignment marking.

9. The alignment device of claim 8 wherein the at least one marking is on a patient's skin at the injection site.

10. The alignment device of claim 9 wherein the injection site is 5 cm cephald to the patient's middle aspect of the medial malleolus and 1 to 2 cm posterior to the patient's tibia.

11. The alignment device of claim 1 wherein the chimney guide is permanently affixed to the wrap proximate the first opening.

12. The alignment device of claim 1 further comprising a needle driver having a housing terminating in a tip, a reciprocating plunger, and a needle channel, and wherein the tip of the needle driver housing is adapted to mate with the first opening to position the needle channel in alignment with the injection site.

13. The alignment device of claim 12 wherein the needle channel of the needle driver is adapted to receive a needle electrode and movement of the reciprocating plunger toward the tip of the housing, when a needle electrode is within the needle channel and the needle channel is aligned with the injection site, causes the needle electrode to be injected into the injection site.

14. The alignment device of claim 1 further comprising a needle driver having a housing terminating in a tip, a reciprocating plunger, and a needle channel, and wherein the tip of the needle driver is adapted to pass through the elevated ring of the chimney guide and mate with the first opening to align the needle channel over the injection site.

15. The alignment device of claim 1 wherein the wrap is a sock-like structure.

16. The alignment device of claim 15 wherein the sock-like structure further comprises a top opening, a bottom opening, a heel opening and an ankle opening.

17. The alignment device of claim 1 wherein the first opening is adapted to be placed over a patient's skin 5 cm cephald to the middle aspect of the medial malleolus and 1 to 2 cm posterior to the tibia.

18. The alignment device of claim 1 wherein the first opening comprises a bore of a tube.

* * * * *